United States Patent [19]

Kummer et al.

[11] 4,071,563
[45] Jan. 31, 1978

[54] MANUFACTURE OF PENT-4-EN-1-AL

[75] Inventors: Rudolf Kummer, Frankenthal; Kurt Schwirten, Ludwigshafen, both of Germany; Hans-Dieter Schindler, deceased, late of Neuried, Germany, by Maria Elisabeth Schindler, heir-at-law; by Ute Lang nee Schindler, heir-at-law, Neuried; by Rainer Schindler, heir-at-law, Hechendorf, both of Germany

[73] Assignee: BASF Aktiengesellschaft, Ludwigshafen (Rhine), Germany

[21] Appl. No.: 669,844

[22] Filed: Mar. 24, 1976

[30] Foreign Application Priority Data

April 19, 1975 Germany .....................2517447

[51] Int. Cl.$^2$ ............................................. C07C 47/20
[52] U.S. Cl. ................................................. 260/601 R
[58] Field of Search ............................ 260/601 R, 600

[56] References Cited

U.S. PATENT DOCUMENTS 3,928,459  12/1975  Mercier ........................... 260/601 R

OTHER PUBLICATIONS

Webb et al., "Jour. Chemical Society" (1961), pp. 4092–4095.

Primary Examiner—Bernard Helfin
Assistant Examiner—W. B. Lone
Attorney, Agent, or Firm—Keil, Thompson & Shurtleff

[57] ABSTRACT

Pent-4-en-1-al is manufactured by passing an acetaldehyde-acetal of the general formula

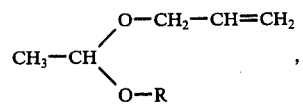

where R is allyl or alkyl of 1 to 3 carbon atoms, in the gas phase and at from 350° to 450° C, over an active-surface catalyst.

6 Claims, No Drawings

MANUFACTURE OF PENT-4-EN-1-AL

The present invention relates to a new process for the manufacture of pent-4-en-1-al

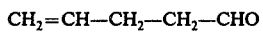

The manufacture of this intermediate, which is of importance for organic syntheses, in a two-state reaction by heating acetaldehyde-diallyl-acetal in the presence of phosphoric acid, followed by thermal rearrangement of the allyl vinyl ether formed, has been disclosed (J. Chem. Soc., 1961, page 4,092 et seq.). However, this technically involved process gives pentenal, together with polymeric materials which are difficult to remove, intotal yields of only about 40%.

It is an object of the present invention to provde a technically and economically more attractive method of obtaining pent-4-en-1-al.

We have found that this object is achieved and that pent-4-en-1-al is obtained in a simple manner, and in high yields, by the unusual reaction which occurs when an acetaldehyde-acetal of the general formula I

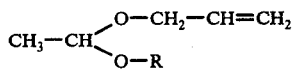

where R is allyl or alkyl of 1 to 3 carbon atoms, is passed, in the gas phase and at from 350° to 450° C, over an active-surface catalyst.

The preferred starting material I is the diallyl-acetal of acetaldehyde. However, the methyl-allyl-acetal, ethyl-allyl-acetal and propyl-allyl-acetal can also be used. These acetals may be obtained in the conventional manner by acetalization of acetaldehyde with a single alcohol or a mixture of alcohols.

Our work to date indicates that the chemical nature of the active-surface catalyst has no significant influence on the reaction, which is primarily a heterogeneous thermolysis of a gaseous material in contact with a solid. Suitable active-surface materials are therefore activated carbon, degassed coal (coke), aluminum oxide, titanium dioxide, pumice and silica. Other oxidic catalysts, which are usually more expensive, such as iron oxide and zinc oxide, can also be used, provided they do not have oxidative properties, such as those of, eg., vanadium oxides and chromium oxides. Aluminum oxide and, quite generally, oxide catalysts, have proved to be particularly suitable.

If acetaldehyde-diallyl-acetal is used as the starting material, allyl alcohol is split off during the reaction and this tends to rearrange to propionaldehyde under the reaction conditions. It is true that propionaldehyde is also a valuable product, but in the present case its formation is undesirable because it affects the economics of the process. We have found that this rearrangement can be suppressed if chemically inert catalysts, such as carbon, are used. Instead of the latter, it is also possible to use other materials which have been deactivated - to suppress propionaldehyde formation - by means of a thin layer of carbon, eg. in the form of carbon black, accounting for from 0.1 to 4% of the catalyst. Such deactivation incidentally occurs automatically over a period of operation, since some carbon is formed anyway in the thermolysis of organic materials and this precipitates on the catalyst. Here again, particularly good results are achieved with aluminum oxide as the catalyst material.

The reaction may be carried out either in contact with a fixed catalyst or in a fluidized bed.

In the fixed bed process, the catalyst is preferably in the form of spherical or approximately spherical particles of diameter from 3 to 8 mm. In order substantially to suppress side-reactions, it is advisable to avoid excessive mean times of contact of the acetals I with the catalyst. Gas flow rates of from 10 to 300 L per hour, preferably from 30 to 100 L per hour, have proved suitable; the gas may consist of I alone, or of mixtures of from 30 to 90% of I with inert gases such as nitrogen or carbon dioxide.

To achieve from 20 to 50% conversion per pass, as has proved desirable, catalyst beds which are from about 20 to 100 cm deep are necessary at the above preferred flow rates. The cross-sectional area of these beds is proportional to the required capacity. Per kilogram of I per hour, this area is from about 10 to 100 cm². For reasons of heat conduction, it is preferred to use, instead of coherent beds of large cross-sectional area, several fixed bed columns each of from 10 to 50 cm² cross-sectional area.

In principle, the foregoing also applied when the process is carried out in a fluidized bed. Taking into account the preferred particle sizes of from 0.1 to 0.8 mm, the stated preferred flow rates and the stated preferred conversions per pass, the fluidized beds are peferably from 5 to 40 cm deep. At cross-sectional areas of from 10 to 100 cm², as are common in fluidized bed technology, these figures correspond to capacities of from 0.04 to 0.8 kg of I per hour.

Both procedures, which are carried out at atmospheric pressure or, preferably, a pressure of from 20 to 400 mbar, are the same as conventional fixed or fluidized bed methods for catalytic processes, present no particular problems and can easily be optimized, from case to case, by a series of preliminary experiments.

After completion of the reaction in contact with the catalyst, the gases are condensed fractionally, the pentenal being obtained in a yield of from about 90 to 98%, based on conversion. If acetaldehyde-diallyl-acetal is used as the starting material, the corresponding amount of allyl alcohol is obtained as a further process product, which, depending on the nature of the catalysts, rearranges, to the extent of from about 5 to 40%, to propionaldehyde. The acetals I and the alcohols ROH split off are recycled to the process.

Pent-4-en-1-al is a valuable intermediate for organic syntheses of all kinds. If, eg., the compound is hydroformlyated, hexane-1,6-dial is obtained and this can be further converted, by simple methods, to hexane-1,6-diol, to adipic acid and to hexamethylenediamine, which are known to be compounds of very great importance in the manufacture of plastics.

EXAMPLE 1

30 L (S.T.P.) per hour of a gas mixture of 75% by volume of acetaldehyde-diallyl-acetal and 25% by volume of nitrogen were passed at 380° C and a pressure of 200 mm Hg, through a tube having a height of 80 cm and a cross-sectionalarea of 19 cm², and which is filled with spherical (diameter 5 mm) aluminum oxide pellets. On working up the reaction mixture by conventional distillation methods, pent-4-en-1-al was obtained in a yield of 89%, based on a conversion of 48%. 28% of the allyl alcohol formed as a by-product had undergone rearrangement to propionaldehyde.

EXAMPLE 2

30 L (S.T.P.) per hour of the gas mixture mentiond in Example 1 were passed, at from 380° to 400° C and a pressure of 40 mm Hg, through a fluidized bed having a depth of 10 cm and a cross-sectional area of 19 cm², and containing 100 ml of fine granules of aluminum oxide (mean particle diameter 0.2 mm). The conversion was 80% and the yield of pent-4-en-1-al, based on this conversion, was 91%. 38% of the allyl alcohol had undergone rearrangement to propionaldehyde.

EXAMPLE 3

On following the method described in Example 2, but using an aluminum oxide on which a little carbon black (about 2% by weight) had been deposited, a somewhat lower conversion (47%) was achieved, but the yield of pent-4-en-1-al was higher (94%), and only 8% of propionaldehyde was formed.

EXAMPLE 4

Following the method described in Example 2, but using acetaldehyde-methyl-allyl-acetal and working at 360° C and atmospheric pressure, a conversion of 87% was achieved. The yield of pent-4-en-1-al was 80%.

We claim:
1. A process for the manufacture of pent-4-en-1-al, wherein an acetaldehyde-acetal of the general formula

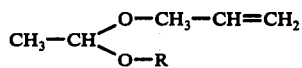

where R is allyl or alkyl of 1 to 3 carbon atoms, is passed in the gas phase and at from 350° to 450° C, over a non-oxidizing, active-surface, particulate catalyst selected from the group consisting of activated carbon, coke, pumice, silica, aluminum oxide, titanium dioxide, zinc oxide and aluminum oxide on which a thin layer of carbon has been applied.

2. A process as claimed in claim 1, wherein aluminum oxide is used as the catalyst.

3. A process as claimed in claim 1 wherein said active-surface catalyst comprises aluminum oxide particles on which a thin layer of carbon has been applied.

4. A process as claim in claim 1 wherein said acetaldehyde-acetal is the diallyl acetal of acetaldehyde.

5. A process as claimed in claim 1 wherein said acetaldehyde-acetal is acetaldehyde-methyl-allyl-acetal.

6. A process as claimed in claim 1 wherein said active-surface catalyst is activated carbon, silica or coke.

* * * * *